United States Patent [19]

Zlokarnik

[11] 4,162,970
[45] Jul. 31, 1979

[54] INJECTORS AND THEIR USE IN GASSING LIQUIDS

[75] Inventor: Marko Zlokarnik, Cologne, Fed. Rep. of Germany

[73] Assignee: Bayer Aktiengesellschaft, Leverkusen, Fed. Rep. of Germany

[21] Appl. No.: 818,893

[22] Filed: Jul. 25, 1977

[30] Foreign Application Priority Data

Jul. 31, 1976 [DE] Fed. Rep. of Germany ....... 2634494

[51] Int. Cl.² .......................... C02B 3/08; C02C 1/12
[52] U.S. Cl. .................................. 210/15; 210/63 R; 210/220; 261/77; 261/78 A; 261/DIG. 75
[58] Field of Search ..................... 137/604; 210/14, 15, 210/60, 63 R, 194, 197, 220, 221 R; 239/428.5, 433, 434.5; 261/77, 78 A, 123, DIG. 75; 366/167, 172, 173; 417/174

[56] References Cited

U.S. PATENT DOCUMENTS

| Re. 20,488 | 8/1937 | Zinkil ................................ 239/428.5 |
| 1,417,146 | 5/1922 | Dederich et al. ................. 261/78 A |
| 2,272,818 | 2/1942 | Petroe ................................ 261/77 X |
| 2,883,169 | 4/1959 | Daman ................................. 261/77 |
| 3,938,738 | 2/1976 | Nagel et al. .................. 239/428.5 X |

FOREIGN PATENT DOCUMENTS 561395  2/1933 Fed. Rep. of Germany ............. 261/77
2401466 7/1975 Fed. Rep. of Germany ........... 210/220

Primary Examiner—Robert H. Spitzer
Attorney, Agent, or Firm—Sprung, Felfe, Horn, Lynch & Kramer

[57] ABSTRACT

In an injector for the dispersion of a gas into a liquid and comprising a gas inlet, a liquid inlet, and a mixing chamber communicating with said inlets and having an inlet and an outlet, the improvement wherein the inlet of said mixing chamber is substantially round in cross-section and the outlet is substantially slit-shaped, whereby the kinetic energy of propulsion can be utilized with high efficiency to produce very fine gas bubbles. Advantageously the cross-sectional area at the outlet of the mixing chamber is about 5 to 25 times the cross-sectional area of the liquid nozzle throat, the liquid nozzle has a throat diameter d diverging to its discharge at an angle of about 5° to 10°, the mixing chamber beginning at a distance from about 1 to 3 d from the end of the inlet, the inlet of the mixing chamber being circular of a diameter of about 3 d, the mixing chamber having a length of about 5 d to 20 d, and the height of the slit being about 1 d. The injector is especially suited for use in treating liquid effluents and in fermentation processes.

5 Claims, 2 Drawing Figures

INJECTORS AND THEIR USE IN GASSING LIQUIDS

In order to intensify mass transfer in a gas-liquid system amongst other things, two-component nozzles such as injectors, ejectors discharge nozzles and venturi nozzles, etc. are employed. In all of these devices, the kinetic energy of the liquid jet (hereafter called the propulsion jet) is used for the dispersion of gas throughput into bubbles which are as fine as possible. Such devices are being increasingly used as gas distributors in bubble columns and particularly for supplying biological waste water or fermentation plants with gases containing oxygen (See German Offenlegungsschriften Nos. 2,400,416, 2,404,289, 2,408,064, 2,410,574, 2,516,371 and 2,458,449).

When changing from two-component nozzles with small diameters (propulsion jet nozzles diameter $\leq 10$ mm) to a larger diameter (propulsion jet nozzle diameter $\geq 10$ mm), the disadvantage of considerably lower efficiency in relation to the gas-liquid interface produced, must be taken into account and this is noticeable, for example, in the lower specific oxygen uptake (kg $O_2$/kWh) obtained.

This state of affairs is related to the fact that the circumferential part of the propulsion jet is more involved in the dispersion of the gas than its core. As the propulsion jet diameter increases, the cross-section of the jet increases in proportion to the square thereof, while its circumference increases only linearly, and this causes an increasingly smaller proportion of the kinetic energy of the propulsion jet throughput to be used for the dispersion of the gas in two-component nozzles (cf. M. L. Jackson AIChE J. 10 (1964) 6, 846/842, M. L. Jackson and W. D. Collin, I & EC Process Design and Develop. 3 (1964) 4, 386/393).

The object of the present invention is to design new injectors which maintain their efficiency with regard to the gas-liquid interface produced even when the diameter of the propulsion jet nozzle is increased.

The present invention, therefore relates to injectors which are particularly suitable for the intensification of mass transfer in a gas-liquid system because the kinetic energy of the propulsion jet is utilized with a high efficiency to form very fine bubbles in a mixing chamber having a circular inlet cross-section, characterized in that the mixing chamber is so designed that the cross-section of the outlet is slit-shaped.

The present invention also relates to a process for the intensification of mass transfer in a gas-liquid system by contacting a gas with a liquid in such a way that the energy of the propulsion jet is utilized with single objective of forming very fine gas bubbles. This process is characterized by the intimate contacting of a propulsion jet liquid with a gas in at least one mixing chamber having a slit-shaped outlet, at propulsion jet velocities of about 5 to 30 meters per second, wherein the ratio of the gas throughput in $m_N^3$ per hour to the propulsion jet throughput in $m^3$ per hour is about 1 to 20, preferably about 5 to 10.

In order to produce a large interface between the liquid and the gas, it is necessary to disperse the gas in very fine gas bubbles and to ensure that the gas-liquid dispersion is mixed extremely rapidly into the surrounding liquid so that the coalescence of gas bubbles is prevented as far as possible.

The present invention achieves these two objectives by designing the mixing chamber of the injector so that it changes from a preferably circular or oval inlet thereof to a slit-shaped outlet.

According to the invention, this design results in a continuous enhancement of the shear stress rates along the boundary layer of the mixing chamber and has a favourable effect on the production of very fine gas bubbles.

According to the invention, the provision that the mixing chamber has a slit-shaped outlet results in a flat belt of gas-liquid dispersion being expelled. This kind of gas-liquid jet is more easily dispersed in the surrounding liquid than a conventional circular jet and this diminishes the tendency of the gas bubbles to coalesce.

The advantages of this injector mixing chamber design, according to the invention, enables the hereinabove-noted disadvantage of low efficiency attending large injectors to be practically eliminated.

The invention will be further described with reference to the accompanying drawings wherein:

FIG. 1 shows a recommended design of the injector, according to the invention, partly sectioned to show the interior of the injector. In this figure, the numerals have the following meanings:

Figure 1:
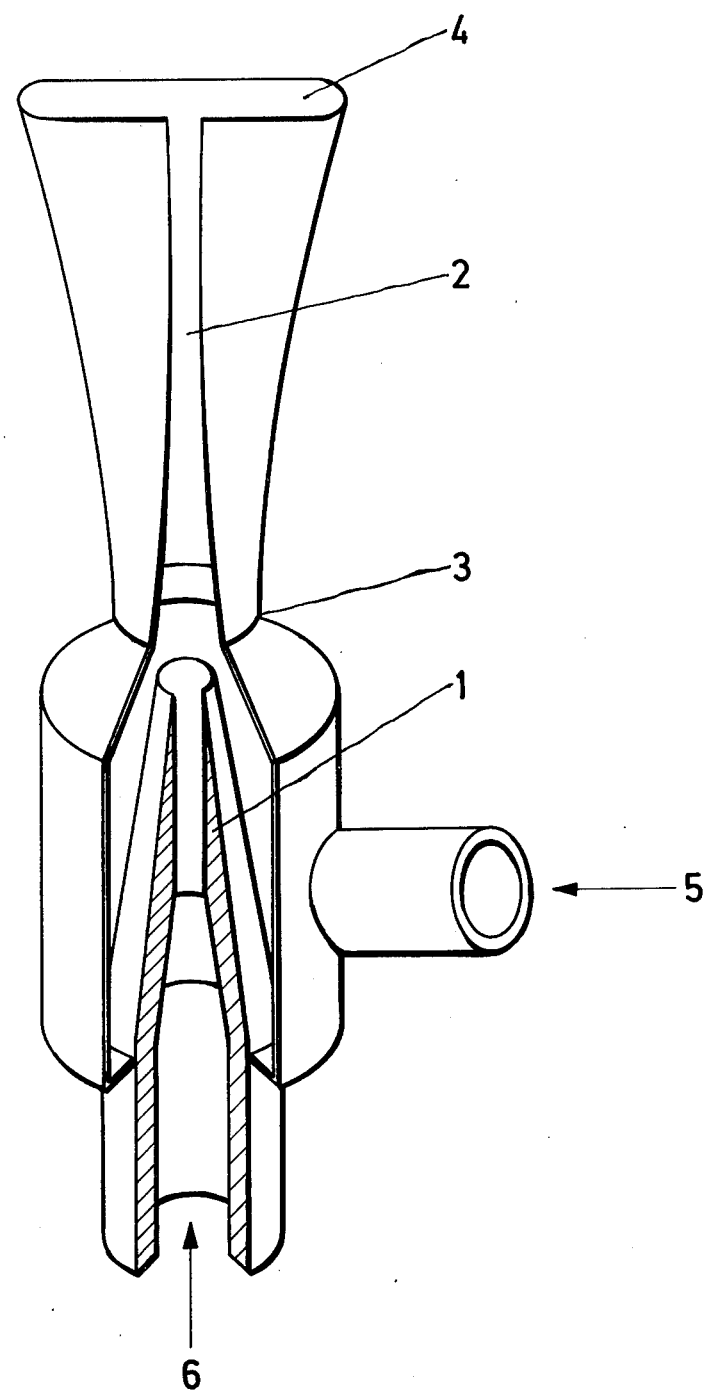
FIG. 1 is a partly sectioned side elevation of an injector in accordance with the invention.

1. Propulsion jet nozzle
2. Mixing chamber
3. Mixing chamber inlet (circular cross-section)
4. Mixing chamber outlet (slit-shaped cross-section)
5. Gas inlet
6. Liquid inlet The injector includes a propulsion jet nozzle 1 and a mixing chamber 2. The propulsion jet nozzle has an opening angle of about 5° to 10° to produce an unstable and rough-surfaced liquid jet. Another recommended design of propulsion jet nozzle is for example, one in which the nozzle outlet is oval or slit-shaped, in order to provide a better match between the liquid jet and the mixing chamber.

Expressed in terms of the throat diameter d of the propulsion jet nozzle, the mixing chamber begins at a distance of about 1 to 3 d from the propulsion jet nozzle, and a recommended mixing chamber design has the following dimensions:

Diameter of the circular mixing chamber inlet: about 3 d;
Length of the mixing chamber: about 5 to 20 d, preferably about 10 to 15 d;
Height of the slit (i.e. smallest diameter) at the outlet of the mixing chamber: about d.

If a mixing chamber having an inlet which is neither circular nor oval is used, then its cross-sectional area at this point should be about 5 to 25 times, preferably about 10 times the cross-sectional area of the propulsion jet throat. In this case the ratio of the longest diameter to the shortest diameter of the cross-sectional area may be between about 1:1 and 3:1, preferably between about 1:1 and 2:1. The cross-sectional area at the outlet of the mixing chamber is about 5 to 25, preferably about 8 to 12 times, the cross-sectional area of the propulsion jet throat. The outlet cross-sectional area of the mixing chamber is also preferably at least as large as the inlet cross-sectional area. At the outlet the ratio of the longest to the shortest diameter may be between about 5:1 and 20:1, preferably between about 5:1 and 10:1. Twisting of the liquid jet within the mixing chamber should be prevented.

Figure 2:
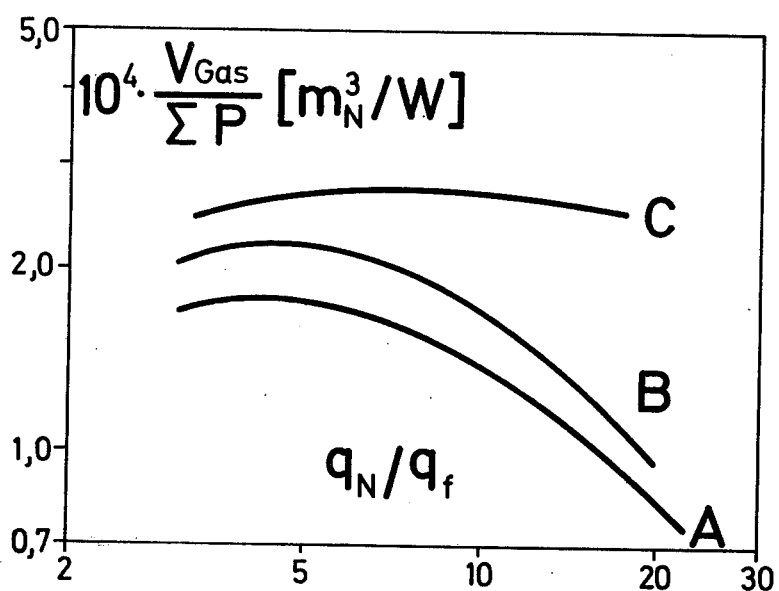
FIG. 2 is the efficiency correlation for three different types of injectors, where the efficiency of the gas-liquid contacting, expressed by standard $m_N^3$ of gas hold-up per unit power in watts is plotted against the ratio of both process parameters.

The efficiency of an injector whose mixing chamber has a shape which is in accordance with the invention, is illustrated in FIG. 2 with results obtained with various types of injectors. These types of injectors were tested under identical conditions as gas distributors in a bubble column having a diameter of 0.60 m and a liquid height of 1.80 m. Three injectors using identical propulsion jet nozzles but different mixing chambers were compared with each other. The nozzle throat diameter was 10 mm and the opening angle was 7°. The length of the mixing chamber was always 14 d and the diameter of the circular inlet was 3 d. The propulsion jet velocity was constant in all measurements, and was 14.2 m/sec at the nozzle throat.

In the case of injector type A, the mixing chamber tapered conically having an outlet diameter of 2 d. In injector type B, according to the invention, the cross-section of the mixing chamber was a continuous transformation from a circular (inlet) to a slit-shaped (outlet) one, having a height of 1 d and an outlet cross-sectional area equal to type A. For the highly recommended injector type C the cross-sectional shape of the mixing chamber was a continuous transformation as in the case of injector type B, so that the slit had a height of 1 d at the outlet, but instead of flattening a pipe of constant cross-section a conical pipe was tapered to a slit so that after flattening the cross-sectional area remained constant over the entire length of the mixing chamber.

If measurements are made using injectors as gas distributors in bubble columns in order to determine their efficiency, gas hold-up in the liquid and the pressure drops of both throughputs are determined at a given liquid height and varying process parameters values, standard gas and liquid throughput. From the pressure drops the net power for compressing the gas and producing the propulsion liquid jet is determined. Now the gas hold-up $V_g$ is related to the sum of power $\Sigma P$ and one obtains an expression for the efficiency of the tested injector which, of course, is a function of the ratio of both process parameters.

FIG. 2 shows the efficiency correlations for the three types of injectors, A, B and C, which were tested. In this figure, the ratio of the two process parameters, standard gas throughput in $m_N^3/h$ and liquid throughput in $m^3/h$, is plotted on the abscissa and the efficiency of the gas-liquid contacting, expressed by standard $m^3$ of gas hold-up per unit power in watts, is plotted on the ordinate.

It can be seen from FIG. 2 that the injector type B is at its optimum about 20% more efficient than the type A injector while both designs have the same inlet and outlet cross-sectional areas, in the injector type B the housing of the mixing chamber converges at a larger angle since the slit height is only d whereas the circular outlet in the injector type A has a diameter of 2 d.

If injector type C is compared with the type B, then at the optimum an increase in efficiency of about 30% is achieved. In both types, the housings of the mixing chamber converge at the same angle, but type C has a smaller gas pressure drop than type B because the cross-sectional area remains constant over the whole length of the mixing chamber.

A particular advantage of the injector type C is that its efficiency is practically independent of the ratio $q_N/q$. Injectors whose efficiency is practically independent of the process parameters can be better suited to the changing process conditions than those whose efficiency is strongly dependent on process parameters.

It will be appreciated that the instant specification and claims are set forth by way of illustration and not limitation, and that various modifications and changes may be made without departing from the spirit and scope of the present invention.

What is claimed is:

1. In a process for intensifying mass transfer in a gas-liquid system by contacting a gas with a liquid utilizing the energy of a propulsion jet to produce very fine gas bubbles, the improvement which comprises passing a liquid through an injector comprising a propulsion jet nozzle, a housing thereabout and a mixing chamber communicating with said housing, said nozzle including a liquid inlet and a throat outlet directed toward the mixing chamber, said housing including a gas inlet, said mixing chamber communicating with said inlets and itself having a round inlet and a substantially slit-shaped outlet of about 5 to 25 times the cross-sectional area of the throat outlet, intimately contacting the gas with a liquid in the mixing chamber, the liquid velocity in the said chamber ranging from 5 to 30 meters per second, the ratio of the gas throughput in $m_N^3$ per hour to the propulsion jet throughput in $m^3$ per hour ranging from about 1:1 to about 20:1.

2. The process according to claim 1, wherein the gas-liquid system is a system for gassing liquid effluent.

3. The process according to claim 2, wherein the ratio of the gas throughput to the propulsion jet throughput is from about 5 to 10.

4. The process according to claim 1, where the gas-liquid system is a system for fermentation.

5. A process according to claim 1, wherein the throat diameter d diverges to its discharge at an angle of about 5° to 10°, the mixing chamber beginning at a distance of about 1 to 3 d from the end of the nozzle, the inlet of the mixing chamber being circular of a diameter of about 3 d, the mixing chamber having a length of about 5 d to 20 d, and the height of the slit-shaped outlet being about d.

* * * * *